(12) United States Patent
Yeh

(10) Patent No.: US 6,347,408 B1
(45) Date of Patent: Feb. 19, 2002

(54) POWDER-FREE GLOVES HAVING A COATING CONTAINING CROSS-LINKED POLYURETHANE AND SILICONE AND METHOD OF MAKING THE SAME

(75) Inventor: Yun-Siung Tony Yeh, Libertyville, IL (US)

(73) Assignee: Allegiance Corporation, McGaw Park, IL (US)

( * ) Notice: Subject to any disclaimer, the term of this patent is extended or adjusted under 35 U.S.C. 154(b) by 0 days.

(21) Appl. No.: 09/186,850

(22) Filed: Nov. 5, 1998

(51) Int. Cl.⁷ ............................................. A41D 19/00
(52) U.S. Cl. .............................. 2/167; 2/161.7; 2/168; 428/35.7; 428/36.8; 428/36.91; 428/451; 428/492; 428/500; 428/521; 428/523; 525/102; 525/103; 525/105; 525/106; 525/127; 525/131
(58) Field of Search ................. 428/35.7, 36.8, 428/36.9, 36.91, 492, 500, 521, 523, 451; 2/161.7, 167, 168; 525/102, 103, 105, 106, 127, 131; 264/112

(56) References Cited

U.S. PATENT DOCUMENTS

| | | | |
|---|---|---|---|
| 4,302,852 A | 12/1981 | Joung | 2/167 |
| 4,304,008 A | 12/1981 | Joung | 2/167 |
| 4,670,330 A | 6/1987 | Ishiwata | 428/290 |
| 4,901,372 A | 2/1990 | Pierce | 2/167 |
| 4,925,668 A | 5/1990 | Khan et al. | 424/422 |
| 5,014,361 A | 5/1991 | Gray | 2/167 |
| 5,020,162 A | 6/1991 | Kersten et al. | 2/164 |
| 5,037,865 A | 8/1991 | Yoshikawa et al. | 523/402 |
| 5,088,125 A | 2/1992 | Ansell et al. | 2/167 |
| 5,165,114 A | 11/1992 | Dams et al. | 2/168 |
| 5,246,996 A | 9/1993 | McVie et al. | 524/265 |
| 5,272,012 A | 12/1993 | Opolski | 428/423.1 |
| 5,272,771 A | 12/1993 | Ansell et al. | 2/167 |
| 5,317,759 A | 6/1994 | Pierce | 2/161.7 |
| 5,335,373 A | 8/1994 | Dangman et al. | 2/161.7 |
| 5,397,824 A | 3/1995 | Mcvie et al. | 524/265 |
| 5,534,350 A | 7/1996 | Liou | 428/423.1 |
| 5,612,083 A | 3/1997 | Haung et al. | 264/233 |
| 5,644,798 A | 7/1997 | Shah | 2/167 |
| 5,742,943 A | * 4/1998 | Chen | 2/168 |
| 5,997,969 A | * 12/1999 | Gardon | 428/35.7 |
| 5,998,540 A | * 12/1999 | Lipkin et al. | 524/591 |

FOREIGN PATENT DOCUMENTS

| | | | |
|---|---|---|---|
| EP | 0 815 880 A2 | 7/1998 | A61L/31/00 |
| WO | WO 9943739 A | * 9/1999 | |

* cited by examiner

*Primary Examiner*—Harold Pyon
*Assistant Examiner*—Sandra M. Nolan
(74) *Attorney, Agent, or Firm*—Andrew G. Rozycki; Donald O. Nickey

(57) ABSTRACT

Powder-free natural rubber and synthetic elastomer gloves having an inner coating of a cross-linked polyurethane impregnated with silicone and their method of manufacture are described. The gloves exhibit good grippability, good donnability as measured by their wet and dry coefficient of friction, tensile strength, elongation to break and stress at 500% modulus.

6 Claims, No Drawings

POWDER-FREE GLOVES HAVING A COATING CONTAINING CROSS-LINKED POLYURETHANE AND SILICONE AND METHOD OF MAKING THE SAME

This invention relates to powder-free natural rubber and synthetic elastomer gloves having an inner coating of a cross-linked polyurethane impregnated with silicone and their method of manufacture. More particularly, the invention relates to unique powder-free medical, surgical or industrial gloves having a silicone impregnated cross-linked polyurethane inner coating which are easy to don and which can be manufactured without manual glove-turning steps during post-processing off-line, such as chlorination, acid rinsing or other treatment processes. Additionally the gloves of the invention exhibit good grippability, good donnability, tensile strength, elongation to break and stress at 500% modulus.

BACKGROUND OF THE INVENTION

Commercially available powder-free natural rubber and synthetic elastomer gloves are typically manufactured by first preparing a powdered glove using conventional latex dipping technology and manufacturing techniques. The gloves are then post-processed off-line to remove powder by chlorination or acid treatment followed by rinsing. Both processes removes powders which have been deposited on the glove during the manufacturing process. The chlorination process also oxidizes the surface of the glove and provides the glove with improved donning characteristics.

These processes have several disadvantages. First of all, they are time and labor-intensive. Chlorination, for example, is a multi-step processs which first requires that the gloves be removed from the former and turned inside out. The gloves are then subjected to several cycles of chlorination, neutralization, rinsing, glove inverting and drying operation steps. In the normal operating cycle for producing powder-free gloves, two manual glove turning steps are required. Since the inner surface or donning side of the glove is the side that is to be chlorinated, the glove must first be turned inside out so that the inner surface of the glove is now on the exterior. After the glove is chlorinated, the glove must then be manually turned again so that the freshly chlorinated donning side is returned to the inner surface of the glove. As a result, post-processing chlorination is also costly.

Another issue associated with chlorination is that the chlorination process may also degrade the polymeric coating applied to the glove's surfaces to render the glove powder free. Generally, the chlorination-associated glove degradation results in poor glove donning, gloves sticking to each other on the coated side, poor coating adhesion and flaking of the coating. Consequently, any polymeric coating applied to the glove surfaces that will be subsequently chlorinated to render the glove powder-free must possess excellent resistance to degradation by chlorination.

SUMMARY OF THE INVENTION

The present invention provides a powder-free, inner-coated, natural rubber or synthetic elastomer glove for medical, surgical and/or industrial applications which has good donning characteristics and good grippability (as measured by the coefficient of friction of the donning and gripping surfaces). The glove of the invention also exhibits good tensile strength, stress at 500% modulus and elongation to break. The gloves can also be manufactured without costly glove-turning steps in the post-processing chlorination.

The inner coating on the gloves of the invention is a cross-linked polyurethane which has been impregnated with a silicone. The inventive gloves have improved donnability over gloves coated on their inner surface with a non-cross-linked polyurethane. The inventive gloves also have improved donnability as compared to gloves with an inner coating of cross-linked polyurethane which does not contain silicone. The polymeric coating of the inventive gloves also exhibits excellent adhesion to the natural rubber or synthetic elastomer rubber and can be chlorinated without being significantly degraded by the chlorination process.

PREFERRED EMBODIMENTS OF THE INVENTION

The gloves of the invention are comprised of a natural rubber, nitrile, polychloroprene, polybutadiene, polyvinylchloride, polyurethane, polyisoprene, styrene diblock and triblock copolymers, or other synthetic elastomers, including blends thereof, which have on their inner surface a coating comprised of a cross-linked polyurethane impregrated with silicone.

The natural rubber may be compounded with stabilizers, a crosslinker, a vulcanization activator, a vulcanization accelerator, an antioxidant, an antiozonant and optionally, white pigment.

Suitable stabilizers include oleates, stearates, alginates, polyacrylates, xanthan gums, caseinates or other nonionic and ionic surfactants. Typical crosslinkers which may used in the compounding formulation include sulfur or other organic peroxides. Suitable vulcanization activators include metal oxides, such as magnesium oxide, lead oxide, and preferably, zinc oxide. The vulcanization accelerator may be chosen from mercaptobenzothiazoles and their derivatives, dithiocarbamates and their derivatives, sulfur donors, guanidines and aldehyde-amine reaction products. Suitable antioxidants include hindered arylamines or polymeric hindered phenols. Typical antiozonants which may be used in the compounding formulation include paraffinic waxes, microcrystalline waxes and intermediate types of waxes (which are blends of both paraffinic and microcrystalline waxes). Typical white pigments that may be used include titanium dioxide and zinc oxide.

Synthetic diene based elastomers such as polybutadiene, polyisoprene, nitrile, polychloroprene and its blends can be compounded with similar compounding ingredients as set forth above. Other synthetic thermoplastic elastomeric materials used for the base glove such as polyvinylchloride, polyurethanes, styrene diblock and triblock copolymers and its blends do not require crosslinking to prepare a glove with the desired physical properties. Accordingly, these synthetic elastomers may be compounded with stabilizers, antioxidants, antiozonants and color pigments as described above.

Those skilled in the art will readily be able to vary the compounding ingredients in the dipping formulation to suit the particular elastomers used to form the base glove as well as the final article desired. It will also be understood by those skilled in the art that the specific chemicals or compounds which have been listed above are representative of conventional materials that may be used in formulating diene-based and thermoplastic elastomers and are non-limiting examples of each such component of the formulation.

The polyurethane dispersion used to coat the interior surface of the formed glove is a crosslinkable anionic polyurethane dispersion with a particle size of less than about 0.5 micron, preferably less than about 0.1 micron with carboxylic acid functionality having an acid value of more than about 15 calculated based on the amount of carboxylic acid-containing material used in synthesizing the polyurethane (assuming total incorporation of the carboxylic acid functionality in the monomer into the finished polymer). Preferably, the polyurethane dispersion is a dispersion blend of [A], a crosslinkable anionic polyester-based polyurethane with a Sward hardness of about 74 or greater (wherein the Sward hardness is measured using ASTM D2134) and an acid value of about 24 or less and [B] a self-crosslinkable anionic polyester-based polyurethane with a Sward hardness of about 38 or less and an acid value of about 24 or greater. The self-crosslinkable polyurethane of the invention is a polyurethane with functionality that can be readily cross-linked using heat, radiation or chemical means with or without the use of external crosslinkers. Most preferably, the polyurethane dispersion is a dispersion blend of [A] about 50 parts of a crosslinkable anionic polyester-based polyurethane with a Sward hardness of about 74 or greater and an acid value of about 24 or less and [B] about 50 parts of a self-crosslinkable anionic polyester-based polyurethane with a Sward hardness of about 38 or less and an acid value of about 24 or greater.

The polyurethane dispersion and blend described above is normally a commercial grade that is provided by the manufacturer with added surfactants and stabilizers. The dispersion may also contain residual solvent and unreacted monomers. For use as part of the coating on the interior of the gloves of the invention, the polyurethane dispersion is additionally compounded with stabilizers, wetting agents, crosslinker, silicone emulsion and optionally, white pigment.

The stabilizers may be oleates, stearates, alginates, caseinates, xanthan gums, polyacrylates or other ionic and nonionic surfactants. Preferably, the stabilizers are nonionic surfactants. Most preferably, the surfactant is a branched nonylphenoxypoly(ethyleneoxy)ethanol. Stabilizers are added to the coating dispersion to improve its stability and to prevent coagulation of the dispersion by contaminating ionic species leached from the latex gloves into the coating dispersion. These additional stabilizers may be omitted if the polyurethane dispersion as received from the manufacturer contains sufficient added stabilizer such that self-coagulation of the dispersion does not occur during glove manufacture.

The wetting agent may be nonionic or ionic surfactants. Preferably, the wetting agent is nonionic or ionic silicone based surfactants. Most preferably, the wetting agent is a nonionic polyether modified silicone surfactant.

The silicone emulsion is a siloxane based silicone emulsion. Preferably, the silicone is a poly(alkylsubstituted siloxane) emulsion. Most preferably, the silicone emulsion is a poly(dimethylsiloxane) emulsion.

The crosslinker may be zirconium, aziridines and melamine-formaldehyde based compounds, generally used as crosslinkers for anionic polyurethanes. Preferably, the crosslinker is a zirconium-based crosslinker. Most preferably, the crosslinker is an ammonium zirconyl carbonate. The dispersion may optionally contain metal oxides, such as zinc oxide and magnesium oxide which also function as crosslinkers and as white pigments.

The compounding ingredients used to prepare the polyurethane-based powder free dispersion and their relative proportions are set forth below in Table I. The total amount of [A] and [B] will be about 100 parts.

TABLE I

| DISPERSION INGREDIENT | DRY OR ACTIVE PARTS BY WEIGHT |
| --- | --- |
| Polyurethane dispersion [A] | About 0 to about 100 |
| Polyurethane dispersion [B] | About 100 to about 0 |
| Wetting Agent | About 0.05 to about 5 |
| Silicone emulsion | About 0.5 to about 20 |
| Cross-linker | About 0.5 to about 10 |
| Stabilizers (optional) | About 0.05 to about 5 |
| Metal Oxides (optional) | About 0.5 to about 10 |

Those skilled in the art will readily be able to vary the compounding ingredients in the dipping formulation to suit the final synthetic or natural rubber article desired. It will also be understood by those of skill in the art that the specific chemicals or compounds which have been listed above are intended to be representative of conventional materials that may be used in preparing the formulation and are merely intended as non-limiting examples of each such component of the formulation.

The polyurethane-based powder-free dispersion can be used to coat the interior of a variety of natural rubber and synthetic elastomer articles, including surgical and examination gloves, industrial gloves, finger cots, tubing, protective coverings, condoms or similar products.

Comparative testing was conducted to evaluate the effect of the different ingredients in the powder-free coating composition on the donnability of the gloves (as measured by the coefficient of friction where the lower the coefficient of friction, the better the donnability). The gloves in the comparative examples were prepared as follows. A glove former was preheated in an oven at about 158° F. for about 2 minutes. The former was then dipped in a water-based coagulant comprised of calcium nitrate, calcium carbonate, wetting agent and water maintained at about 122° F. The former with the coagulant layer was then dried in the oven at 158° F. for about 3 minutes. The coagulant-coated former was dipped into a compounded natural rubber latex and allowed to remain there for about 2 to about 10 seconds. The former bearing the coagulated latex film was then removed from the latex and leached in a warm water bath held at about 122° F. for about 5 minutes. The former bearing the latex film was then dipped into a powder free coating dispersion containing the ingredients set forth in Table 2 below.

The former was then placed in an oven at 248° F. for about 20 minutes to cure the coated latex film. The gloves were then stripped from the former and tested for adhesion and coefficient of friction.

The powder free coating dispersion in these examples comprises a polyurethane blend, wetting agent, silicone emulsion and crosslinker as indicated in Table 2. The polyurethane blend used in all examples was comprised of 50 dry parts of [A] an anionic polyester-based polyurethane with a Sward hardness of about 74 and an acid value of about 21.6 and 50 dry parts of [B] an anionic polyester-based polyurethane with a Sward hardness of about 38 with an acid value of about 26.7. The silicone emulsion was 11.1 dry parts of SM 2140, a polydimethylsiloxane dispersion available from General Electric. The crosslinker was 3.3 dry parts of Bacote 20, an ammonium zirconyl carbonate compound from Magnesium Elektron Inc., Flemington, N.J., and the wetting agent was 0.56 parts of BYK 348, a polyether-modified siloxane available from BYK-Chemie. The total solid content (TSC) was adjusted to about 2.5% to about 3.0% by adding water.

The coefficient of friction (COF) measurements were performed following the procedure set forth in ASTM D1894-95 except for the wet COF determination. Test samples were cut from the palm area of each glove and were taped to the sled using adhesive tape so that the tapes did not come into contact with the friction fixture surface. To measure wet COF, 10–20 ml of distilled water was added onto the friction fixture surface and the sled with the wrapped sample films was placed onto the wet fixture. The wet kinetic COF was calculated by dividing the average of the load force over the travel distance by the weight of the sled. The relative effects on the coefficient of friction of the different ingredients in the powder-free dispersion are illustrated in Table 2 below.

TABLE 2

| Powder-Free Dispersion | PU Blend | PU Blend/Silicone | PU Blend-Silicone-Wetting Agent-Bacote 20 |
|---|---|---|---|
| TSC (weight %) | 2.5 | 2.5 | 2.5 |
| Dry COF | 1.169 | 0.515 | 0.370 |
| Wet COF | 0.830 | 0.741 | 0.638 |

Table 2 shows that the coefficient of friction of a glove surface coated with the powder-free coating disclosed in the invention, i.e. crosslinked polyurethane impregnated with silicone is significantly superior to those comparative example gloves that were coated with an uncross-linked polyurethane blend alone or uncross-linked polyurethane blend/silicone.

Comparative testing also demonstrates that the lowest coefficient of friction for the inventive gloves was obtained when Bacote 20 was used as the cross-linker. These results are summarized below in Table 3 where each entry represents a glove prepared by coating the interior of the glove with a polyurethane dispersion comprised of a polyurethane blend, wetting agent, silicone and crosslinker at a total solid content (TSC) of 2.5% to yield a glove with an inner coating comprised of a crosslinked polyurethane impregnated with silicone. Cymel 325 is a methylated melamine-formaldehyde available from Cytec Industries, Inc., and QZ-43 is a polyfunctional aziridine available from K. J. Quinn and Co, Inc.

TABLE 3

| Crosslinker | Bacote 20 | Cymel 325 | QZ-43 |
|---|---|---|---|
| Dry COF | 0.370 | 0.572 | 0.554 |
| Wet COF | 0.638 | 0.803 | 0.882 |

The adhesion of the coating was also evaluated qualitatively. In this test, the coated glove surface was stretched to more than 500% and the coating was rubbed repeatedly using the thumb. The coated surface was then visually examined for coating flakes and powdery substances. The adhesion of the coating was rated qualitatively on a scale of 1 to 5, 1 being the worst with the entire coating flaking off the rubber substrate and 5 being the best with no visual appearance of powdery substance on the surface of the glove. Using this test, the adhesion of the inventive coating is quite good with a rating of 4 to 4.5 on a scale of 5 (where about 4 to about 4.5 is the adhesion value exhibited by commercially available glove coatings)

The gloves fabricated in accordance with the present invention may be prepared as follows. A mold in a contoured shape of a glove is first oven dried and then dipped into an alcohol or water-based coagulant dispersion comprising calcium nitrate, powder (calcium carbonate or cornstarch), wetting agent and water or alcohol (for alcohol based coagulant dispersion). The coagulant layer deposited on the glove former is then dried. The glove former is then dipped into the compounded natural rubber or synthetic elastomer and a film of the rubber or synthetic elastomer is coagulated on the glove former. While still on the former, the layer of coagulated natural rubber or synthetic elastomer is optionally leached with water and then dipped into a powder-free dispersion comprising a polyurethane dispersion, a wetting agent, a silicone emulsion, a cross-linker, stabilizers and water as set forth in Table 1 above. The former carrying the polyurethane-dispersion coated natural rubber or synthetic elastomer is then cured in an oven. The former is removed from the oven and the coated glove is then stripped from the former.

The gloves are then post-processed by chlorination, acid treatment or other chemical processing to remove the calcium carbonate or cornstarch powder. If the glove has been formed with a bead, the gloves can be chlorinated or acid treated without manual glove turning steps. If powder is removed by chlorination, the gloves may be treated as follows. The gloves are optionally pre-rinsed with water and immersed in an aqueous chlorinated solution (200 ppm chlorine) for about 8 minutes. The chlorinated solution is then neutralized by adding a base, e.g. ammonium hydroxide, to the solution until the pH is about 7 or above. The neutralized solution is then drained and the gloves are rinsed with water for about 2.5 minutes. The gloves are rinsed three more times (for about 2.5 minutes per time) to remove traces of the chlorinated solution and the neutralizing base. Alternatively, the neutralization step may be omitted and the gloves washed with water to remove traces of the chlorinated solution. The rinsed gloves are then placed in an extractor to remove excess water. The gloves are removed from the extractor and placed in a cyclone drier and dried. Alternatively, the gloves may be dried immediately after they are rinsed with water. After the gloves are completely dried, the gloves may be packed.

If powder is removed by acid treatment, the gloves may be treated as follows. The turned gloves are rinsed with an acid solution which may optionally contain detackifiers. The gloves are then rinsed with water to remove traces of water and placed in an extractor to remove excess water. The gloves are removed from the extractor and placed in a cyclone drier and dried. Alternatively, the gloves may be dried immediately after they are rinsed with water. After the gloves are completely dried, the gloves may be packed.

If the powdered coated gloves are not formed with a bead, the following additional glove-forming steps are taken after the curing step described above. After the layers and coating are cured and the former is removed from the oven, the coated glove is optionally dipped into a powder slurry comprising calcium carbonate or cornstarch in water. This powder application step is desirable since there will be an area beneath the rubber or synthetic elastomer dip level which is not coated with polyurethane (to minimize contamination of the former with the polyurethane coating). This uncoated area is tacky and is preferably dusted by powder. Another option is to selectively dust the uncoated layer or rubber or synthetic elastomer with powders using a roller application. The glove is then stripped from the former.

To prepare the powder-free coated gloves, the gloves are post-processed by initially turning the gloves inside out and treating them to remove powder as described above. After the gloves are dried, the gloves are turned inside out again such that the polyurethane-coated surface is inside. The gloves are then dried further before packing.

The gloves of the invention have a thickness of at least about 0.003 inches. Preferably, the thickness of the gloves ranges between about 0.004 inches and about 0.010 inches. Most preferably, the-glove thickness is between about 0.005 and about 0.008 inches.

The gloves of the invention exhibit a tensile strength of greater than about 1300 psi, preferably greater than about 2000 psi and most preferably, greater than about 2600 psi. The stress at 500% of the gloves of the invention is less than about 3000 psi, preferably less than about 2000 psi and most preferably, less than about 1000 psi. The gloves of the invention have an elongation to break greater than about 200%, preferably greater than about 400% and most preferably greater than about 500%.

The gloves of the invention exhibit a dry kinetic COF of less than about 0.5 for the donning (coated) inner surface and greater than about 0.5 for the gripping (uncoated) outer surface. Preferably, the dry kinetic COF is less than about 0.4 for the donning surface and greater than about 0.6 for the gripping surface. Most preferably, the dry kinetic COF is less than about 0.3 for the donning surface and greater than about 0.7 for the gripping surface.

Natural rubber gloves coated on their interior with the polyurethane coating of the invention exhibit a tensile strength of greater than about 2000 psi, preferably greater than about 3000 psi and most preferably, greater than about 4000 psi. The stress at 500% of the polyurethane coated natural rubber gloves of the invention is less than about 2000 psi, preferably less than about 1000 psi and most preferably, less than about 800 psi. The polyurethane coated natural rubber gloves have an elongation to break greater than about 200%, preferably greater than about 500% and most preferably greater than about 800%.

The dry kinetic COF of the polyurethane coated natural rubber gloves is less than about 0.5 for the donning surface and greater than about 0.5 for the gripping surface. Preferably, the dry kinetic COF is less than about 0.4 for the donning surface and greater than about 0.6 for the gripping surface. Most preferably, the dry kinetic COF is less than about 0.3 for the donning surface and greater than about 0.7 for the gripping surface.

Nitrile rubber gloves coated on their interior with the polyurethane coating of the invention exhibit a tensile strenth of greater than about 2000 psi, preferably greater than about 2500 psi and most preferably greater than about 3000 psi. The stress at 500% of the polyurethane coated nitrile gloves of the invention is less than about 3000 psi, preferably less than about 2000 psi and most preferably, less than about 1000 psi. The polyurethane coated nitrile gloves have an elongation to break greater than about 200%, preferably greater than about 400% and most preferably greater than about 500%.

The dry kinetic COF of the polyurethane coated nitrile rubber gloves is less than about 0.5 for the donning surface and greater than about 0.4 for the gripping surface. Preferably, the dry kinetic COF is less than about 0.4 for the donning surface ad greater than about 0.6 for the gripping surface. Most preferably, the dry kinetic COF is less than about 0.3 for the donning surface and greater than about 0.7 for the gripping surface.

Neoprene rubber gloves coated on their interior with the polyurethane coating of the invention exhibit a tensile strenth of greater than about 2000 psi, preferably greater than about 2400 psi and most preferably greater than about 2600 psi. The stress at 500% of the polyurethane coated neoprene gloves of the invention is less than about 2000 psi, preferably less than about 1000 psi and most preferably, less than about 800 psi. The polyurethane coated neoprene gloves have an elongation to break greater than about 200%, preferably greater than about 500% and most preferably greater than about 800%.

The dry kinetic COF of the polyurethane coated neoprene rubber gloves is less than about 0.5 for the donning surface and greater than about 0.5 for the gripping surface. Preferably, the dry kinetic COF is less than about 0.4 for the donning surface ad greater than about 0.6 for the gripping surface. Most preferably, the dry kinetic COF is less than about 0.3 for the donning surface and greater than about 0.7 for the gripping surface.

The glove thickness is measured by a digital thickness gauge and is the average of three measurements in the palm area. Tensile strength, stress at 500% modulus and elongation to break are measured according to ASTM D412-92. Dry kinetic COF and wet kinetic COF are measured according to ASTM D1894-95 and as set forth above.

The invention is further illustrated by the following examples. It is understood that one of ordinary skill in the art will understand how to vary the times and temperatures of the process in accord with the article manufactured, the specific elastomer or blend employed and the particular formulation ingredients selected. Similarly, one of ordinary skill in the art will know how to select a post-processing method compatible with his individual glove manufacturing line and equipment.

EXAMPLE 1

Powder-free natural rubber latex gloves coated on their interior with a cross-linked polyurethane impregnated with a silicone were manufactured by first preheating a glove former in an oven maintained at about 120 to about 180° F. The glove former was then dipped into an alcohol or water-based coagulant dispersion maintained at less than about 140° F. for enough time to allow the coagulant to coat the former. The coagulant dispersion is comprised of calcium nitrate, calcium carbonate powders, wetting agents and water (or alcohol for alcohol based coagulant dispersion). The coagulant layer which had been deposited on the glove former was then allowed to dry.

The glove former with the dried coagulant layer was then dipped into the compounded natural rubber latex which was maintained at about 68 to about 86° F. The glove former was left in the latex formulation for enough time to allow the natural rubber latex to coagulate on the glove former to reach the desired thickness. The glove former was then removed from the latex and the coagulated latex was leached for about 3 to about 10 minutes in a water leaching tank maintained at about 100 to about 160° F.

The glove former carrying the coagulated natural rubber latex was then dipped into a powder-free polyurethane coating dispersion which was maintained at about 68 to about 86° F. for less than about 1 minute.

The powder-free polyurethane coating dispersion was comprised of about 49.7 dry parts of [A], an anionic polyester-based polyurethane with a Sward hardness of about 74 and an acid value of about 21.6, about 50.3 dry parts of [B], an anionic polyester-based polyurethane with a Sward hardness of about 38 with an acid value of about 26.7, about 11.1 dry parts of GE SM2140, about 0.5 part of Igepal CO-730, a branched nonylphenoxypoly(ethyleneoxy) ethanol surfactant available from Rhone-Poulenc, about 0.5 part of BYK 348 and about 2.2 parts of Bacote 20. The total solid content was then adjusted to about 2.0% using soft water.

The gloves were removed from the dispersion and cured while still on the former in an oven at a temperature of about 248° F. for about 10 to about 20 minutes. The gloves were then removed from the oven. The cured polyurethane coated natural rubber latex glove was then dipped into a powder slurry comprising 3% calcium carbonate in water. The powdered coated glove was then removed from the slurry and dried in an oven at a temperature of about 248° F. for about 1 to about 3 minutes. The glove was then stripped from the former.

The gloves were then post-processed by chlorination to remove the calcium carbonate powder. Since the glove dipping line did not include a beader, it was necessary to post-process the gloves with manual turning. The gloves were first manually turned inside-out and were pre-rinsed with water twice for a period of about 5 minutes. The gloves were then immersed in an aqueous chlorinated solution containing about 200 ppm chlorine for about 8 minutes. The chlorinated solution was neutralized by adding ammonium hydroxide to the solution until the pH is about 7 or above. The neutralization process took about 4 minutes. The neutralized solution was then drained from the chlorinator and the gloves were rinsed with water for about 2.5 minutes. The washing step was repeated three more times. The rinsed gloves were then placed in an extractor for about 5 minutes to remove excess water. The gloves were removed to a drier and heated to about 140° F. for about 40 minutes. The gloves were then removed and manually turned. The gloves were again placed in the drier and heated to about 140° F. for about 15 minutes to completely dry. The gloves were then ready for packaging.

The gloves prepared as set forth in Example 1 had an average thckness of about 0.0078 inches, a tensile strength of about 4300 psi, a stress at 500% of about 350 psi and an elongation of about 970%, a dry kinetic COF of about 0.21 to about 0.24 for the coated donning surface and a dry kinetic COF of about 0.49 to about 0.72 for the uncoated gripping side.

EXAMPLE 2

Powder-free natural rubber latex gloves coated on their interior with a cross-linked polyurethane impregnated with a silicone were manufactured by first preheating a glove former in an oven maintained at about 120 to about 180° F. The glove former was then dipped into an alcohol or water-based coagulant dispersion maintained at less than about 140° F. for enough time to allow the coagulant to coat the former. The coagulant dispersion was comprised of calcium nitrate, calcium carbonate powders, wetting agents and water (or alcohol for alcohol based coagulant dispersion). The coagulant layer which had been deposited on the glove former was then allowed to dry.

The glove former with the dried coagulant layer was then dipped into the compounded natural rubber latex which was maintained at about 68 to about 86° F. The glove former was left in the latex formulation for enough time to allow the natural rubber latex to coagulate on the glove former to reach the desired thickness. The glove former was then removed from the latex and the coagulated latex was leached for about 3 to about 10 minutes in a water leaching tank maintained at about 100 to about 160° F.

After leaching, the glove former bearing the leached natural rubber latex was dried in an oven at a temperature of about 230° F. for about 2 minutes. The glove former carrying the natural rubber latex was removed from the oven and then dipped into a powder-free polyurethane coating dispersion which was maintained at about 68 to about 86° F. for less than about 1 minute.

The powder-free polyurethane coating dispersion was comprised of about 49.7 dry parts of [A] an anionic polyester-based polyurethane with a Sward hardness of about 74 and an acid value of about 21.6, about 50.3 dry parts of [B] an anionic polyester-based polyurethane with a Sward hardness of about 38 with an acid value of about 26.7, about 11.4 dry parts of GE SM2140, about 0.5 part of Igepal CO-730, a branched nonylphenoxypoly(ethyleneoxy) ethanol surfactant available from Rhone-Poulenc, about 0.5 part of BYK-348 and about 2.2 parts of Bacote 20. The total solid content was adjusted to about 1.8 to about 2.0% using water.

The coated gloves were then removed from the dispersion and beads were formed using a roller beader. The gloves were cured in an oven at a temperature of about 230° F. for about 10 to about 20 minutes. The cured polyurethane coated natural rubber latex gloves were removed from the oven and stripped from the former.

The gloves were then post-processed by chlorination to remove the calcium carbonate powders. The gloves were immersed in an aqueous chlorinated solution containing about 200 ppm chlorine for about 8 minutes. The chlorinated solution was neutralized until the pH was about 7 or higher. The neutralized solution was then drained from the chlorinator and the gloves were rinsed with water. The washing step was repeated three more times. The rinsed gloves were then placed in an extractor for about 5 minutes to remove excess water. The gloves were removed to a cyclone drier and heated to about 140° F. for about 60 minutes. The gloves were then allowed to cool down to ambient temperature in the cyclone drier for about 15 minutes before they were removed from the drier. The gloves were ready for packaging.

The gloves prepared as set forth in Example 2 had an average thickness of about 0.0067 inches, a tensile strength of about 3870 psi, a stress at 500% of about 609 psi and an elongation to break of about 813%, a dry kinetic COF of about 0.4 for the coated donning surface and a dry kinetic COF of about 1.6 for the uncoated gripping side.

EXAMPLE 3

Powder-free nitrile gloves coated on their interior with a cross-linked polyurethane impregnated with a silicone are manufactured by first preheating a glove former in an oven maintained at about 100 to about 180° F. The glove former is then dipped into an alcohol or water based coagulant dispersion maintained at less than about 140° F. for enough time to allow the coagulant to coat the former. the coagulant dispersion is comprised of calcium nitrate, calcium carbonate powders, wetting agents and water (or alcohol for alcohol based coagulant dispersion). The coagulant larger which had been deposited on the glove former is then allowed to dry.

The glove former with the dried coagulant layer is then dipped into the compounded nitrile latex maintained at about 68 to about 86° F. The glove former is left in the nitrile latex for enough time to allow the nitrile latex to coagulate on the glove former to reach the desired thickness. The glove former is then removed from the nitrile latex and the coagulated latex is leached for about 3 to about 10 minutes in a water leaching tank maintained at about 78 to about 110° F.

The glove former carrying the coagulated nitrile latex is then dipped into a powder-free polyurethane dispersion comprised of a polyurethane blend, silicone, crosslinker, wetting agent, stabilizer and water maintained at about 68 to about 86° F. for less than about 1 minute. The gloves are then removed from the dispersion and beads are formed using a roller bender. The gloves are cured in an oven at a temperature of about 260° F. for about 10 to about 20 minutes. The cured polyurethane coated nitrile gloves are removed from the oven and stripped from the former.

The gloves are then post-processed by chlorination to remove the calcium carbonate powders. The gloves are immersed in an aqueous chlorinated solution containing about 50–100 ppm chlorine for about 8 minutes. The chlorinated solution is neutralized until the pH is about 7 or higher. The neutralized solution is then drained from the chlorinator and the gloves are rinsed with water. The washing step is repeated three more times. The rinsed gloves are then placed in an extractor for about 5 minutes to remove excess water. The gloves are removed to a cyclone drier and heated to about 140° F. for about 60 minutes. The gloves are then allowed to cool down to ambient temperature in the cyclone drier for about 15 minutes before they are removed from the drier. The gloves are ready for packaging.

The gloves prepared as set forth in Example 3 will have an average thickness of about 0.005 to about 0.006 inches, a tensile strength of about 2200 to about 3000 psi, a stress at 500% of about 800 to about 1000 psi and an elongation to break of about 600 to about 750%, a dry kinetic COF of about 0.2 to about 0.4 for the donning surface and a dry kinetic COF of about 0.5 to about 0.7 for the gripping surface.

The foregoing description and examples related only to preferred embodiments of the present invention and numerous changes and modifications may be made therein without departing from the spirit and scope of the invention as defined in the following claims.

What is claimed is:

1. A powder-free elastomeric glove having a coating on an internal surface of the glove, the coating comprising a blend of a crosslinked anionic polyester-based polyurethane with a Sward hardness of about 74 or greater and an acid value of about 24 or less and a crosslinked anionic polyester-based polyurethane with a Sward hardness of about 38 or less and an acid value of about 24 or greater and impregnated with silicone, wherein the glove has a tensile strength of greater than about 1300 psi and a dry kinetic coefficient of friction on the internal surface of the glove less than about 0.5.

2. The glove of claim 1 wherein the glove has a stress at 500% less than about 3000 psi.

3. The glove of claim 2 wherein the glove has an elongation to break greater than about 200%.

4. The glove of claim 3 wherein the glove is a natural rubber glove.

5. The glove of claim 4 wherein the glove is a nitrile rubber glove.

6. The glove of claim 5 wherein the glove is a neoprene rubber glove.

* * * * *